United States Patent
McLardy-Smith

[11] Patent Number: 5,116,379
[45] Date of Patent: May 26, 1992

[54] PROSTHESIS

[76] Inventor: Peter D. McLardy-Smith, 30 Stanley Road, Oxford OX4 1QZ, United Kingdom

[21] Appl. No.: 405,952

[22] Filed: Sep. 12, 1989

[30] Foreign Application Priority Data

Sep. 15, 1988 [GB] United Kingdom ............... 8821574

[51] Int. Cl.⁵ .................................................. A61F 2/34
[52] U.S. Cl. ............................................ 623/23; 623/18
[58] Field of Search ................... 623/10, 18, 19, 20, 623/22, 23

[56] References Cited

U.S. PATENT DOCUMENTS

| | | | |
|---|---|---|---|
| 4,488,319 | 12/1984 | von Recum | 623/23 |
| 4,718,915 | 1/1988 | Epinette | 623/23 |
| 4,718,916 | 1/1988 | Morcher | 623/23 |
| 4,790,852 | 12/1988 | Noiles | 623/23 |
| 4,851,007 | 7/1989 | Gray | 623/23 |

FOREIGN PATENT DOCUMENTS

| | | | |
|---|---|---|---|
| 0038897 | 11/1981 | European Pat. Off. | 623/23 |
| 0170982 | 10/1985 | European Pat. Off. | |
| 0187903 | 10/1985 | European Pat. Off. | |
| 0192996 | 2/1986 | European Pat. Off. | |
| 0179626 | 4/1986 | European Pat. Off. | 623/18 |
| 0257359 | 3/1988 | European Pat. Off. | 623/23 |
| 0307646 | 8/1988 | European Pat. Off. | |
| 2726297 | 12/1978 | Fed. Rep. of Germany | 623/22 |
| 2606273 | 5/1988 | France | 623/22 |
| 2070939 | 9/1981 | United Kingdom | |
| 85/03426 | 8/1985 | World Int. Prop. O. | |

OTHER PUBLICATIONS

*Implant Femoral Visse FEMORA*, Chas. F. Thackray.

*Primary Examiner*—David J. Isabella
*Attorney, Agent, or Firm*—Davis, Bujold & Streck

[57] ABSTRACT

A prosthesis comprising a proximal portion (1) which is shaped to fit within the medullary canal of the metaphysis of the bone and a distal portion (2) shaped to fit within the medullary canal of the diaphysis of the bone. The proximal and distal portions (1,2) are separately formed and fit together by means of a shaft (8) on the distal portion (2) which slides within a hole (7) in the proximal portion (1). The two portions (1,2) may thus be independently selected to provide the desired fit within the bone. Movement of the proximal portion (1) on the stem (8) of the distal portion (2) prevents the latter being forced into a wedge fit with the diaphysis when load is applied to the proximal portion (1). Load transfer between the proximal portion (1) and the metaphysis is thus maintained so avoiding bone resorption.

10 Claims, 3 Drawing Sheets

PROSTHESIS

This invention relates to a prosthesis for implantation in a bone and, more particularly, to the femoral component of an artificial hip joint. It also relates to a method of implanting the prosthesis.

Total hip endoprostheses have been in widespread use for over 20 years. One of the major problems with their use remains the long term fixation of the prosthesis to the bone. The most widely practiced means of fixation has been the use of a bone cement such as polymethylmethacryrlate as a grouting agent between a metal prosthesis and the bone. There are, however, certain disadvantages with this method, the most important being that when the cement fails it tends to fragment and small particles of cement produce an inflammatory response within the tissues which leads to bone resorption.

Over the last 15 years, increasing interest has been focused on the fixation of the prosthesis without the use of cement. This requires an initial tight press fit of the prosthesis into the medullary canal of the bone and various types of surface have been devised such that if bone is laid down against the prosthesis, it provides a rigid interlock. Current thinking is that, provided the initial press fixation is good enough, then bony aposition against the surface is likely to provide adequate long term fixation without the need for a porous coating on the surface of the prosthesis.

Mammalian bone has two primary functions, one to provide a lever arm system by wich the animal can move, and the second to maintain the cells of the blood and the immune system. These two functions are reflected in two structural types of bone: hard cortical bone which takes the majority of the stress (in long bones this is thickest in the midshaft and thinnest at the ends of the bone), and spongy cancellous marrow bone which primarily provides a location for blood cell division. However, trabeculae within the cancellous bone are also able to take stress and their contribution to stress distribution is greatest at the ends of the bone near the joints where the cortical bone is thinnest.

It is known that bone responds to physical forces by being laid down along the lines of stress, so a bone subjected to physiological loading will increase its bone volume and thus its strength. Conversely, a bone that is rested, or subject to no loading, will diminish in bone volume and weaken. All intra medullary femoral prostheses involve the removal of the trabeculae of the cancellous bone around the head and neck of the femur so subsequent stress transfer between the prosthesis and the femur must be into the cortical bone. If the tip of the femoral prosthesis is jammed or wedged into the diaphysis, then stress transfer will occur at this point so the metaphysial cortical bone will be stress shielded and tend to resorb. Ultimately, this will lead to failure of fixation of the implant and the need for revision to another implant. The revision is also rendered technically more difficult because of the poor bone quality in the proximal metaphysis of the femur.

The theoretical solution to this problem is that the proximal part of the prosthesis should be a tight wedge fit in the metaphysis while the distal stem of the prosthesis acts merely as a keel or 'anti-toggle' device by being fitted but not jammed into the femoral diaphysis.

The relative sizes of the metaphysial and diaphysial medullary cavities vary not only between individuals but also within individuals according to age. With advancing years, there is endosteal resorption of the diaphysial cortex leading to cortical thinning and an increase in the diaphysial medullary cavity. Conversely, a large active male, might have a very wide metaphysial medullary cavity but very thick cortices in the diaphysis leading to a very narrow diaphysial medullary cavity. This natural variation is rendered even more complex when the combinations that might result from an already failed previous implant are considered. Here, there may be any combination of bone resorption, proximally or distally.

Prostheses are made in a variety of sizes but as the sizes of the proximal and distal portions are usually increased or decreased in proportion to each other they cannot accomodate the wide range of variations discussed above. Large numbers of different size prostheses thus need to be provided which increases the overall cost of the stock held by a hospital. The present invention aims to overcome these disadvantages and provide further improvement in fixation of the prosthesis.

According to a first aspect of the invention. there is provided a prosthesis for implantation in a bone comprising a proximal portion shaped to fit within the medullary canal of the metaphysis of the bone and to project from the end of the bone and a distal portion shaped to fit within the medullary canal of the diaphysis of the bone, the proximal and distal portions being separately formed and arranged to fit together so they may be independently selected to provide the optimum fit within the bone.

The invention also provides a plurality of proximal and distal protions of different sizes which may be interchangeably fitted together to provide a prosthesis as described above.

According a second aspect of the invention. there is provided a method of implanting such a prosthesis within a bone comprising the steps of: selecting proximal and distal portions to provide the desired fit within the bone and implanting the prosthesis with the two portions fitted together such that the proximal portion fits within the medullary canal of the metaphysis of the bone and the distal portion fits within the medullary canal of the diaphysis of the bone.

Preferred features of the invention will be apparent from the subsidiary claims of the specification and from the following description.

The invention will now be further described, merely by way of example, with reference to the accompanying drawings, in which.

Although the invention is described in relation to the femoral component of an artificial hip joint, it will be appreciated that it is also applicable to prostheses for other types of joint. Similarly, it is applicable to prostheses used in animals or humans.

Figure 1:
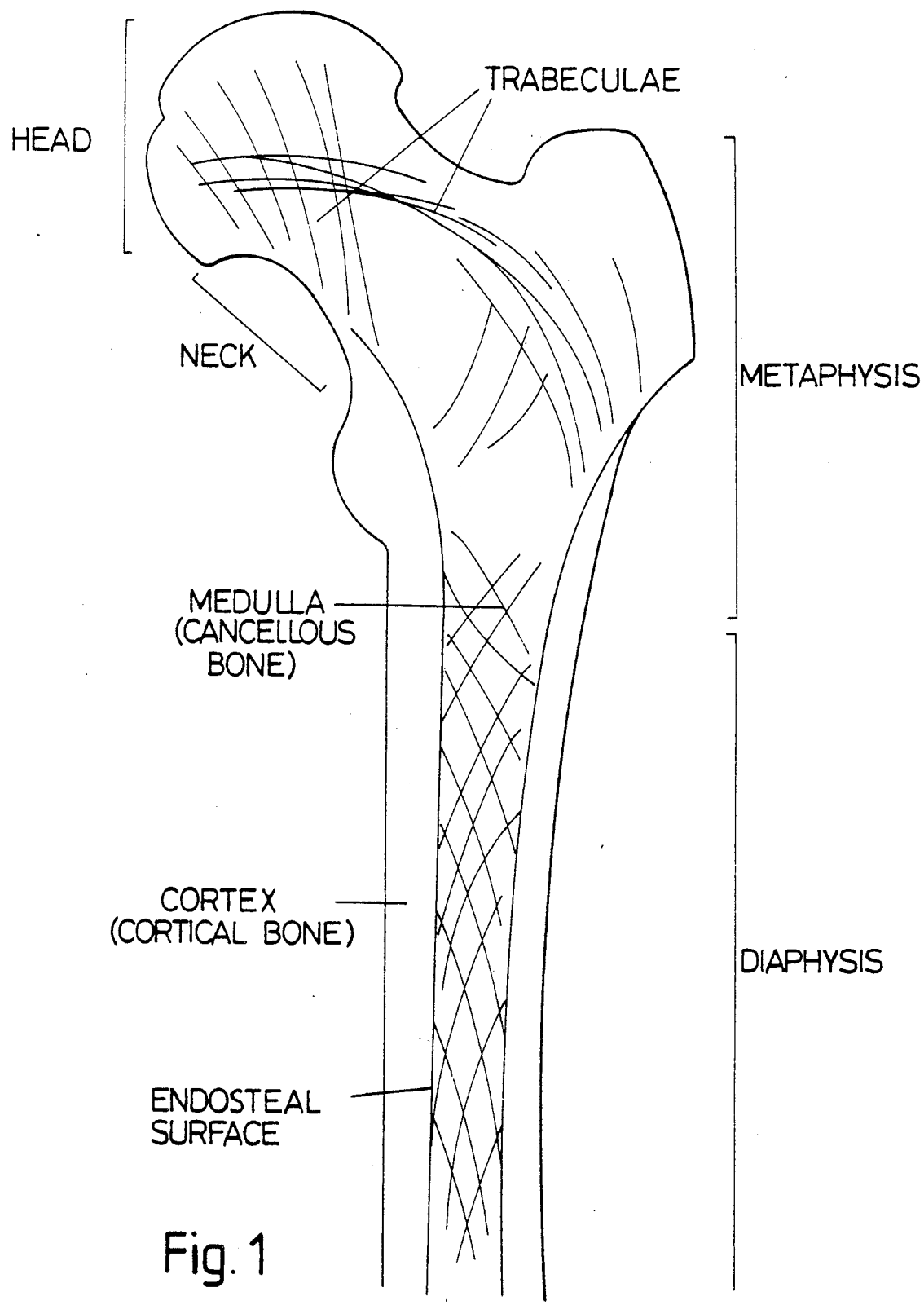
FIG. 1 shows the upper end of a femur.

FIG. 1 shows the parts forming the upper end of a femur mentioned in the discussion of the prior art given above. The figure shows the head and neck of the femur and indicates the metaphysial and diaphysial portions of the bone. The cortex (cortical bone), medulla (cancellous bone) and the trabeculae are also indicated. The endosteal surface between the medullary canal and the cortex is also shown.

FIG. 2 illustrates an embodiment of a prosthesis according to the invention. Since, as discussed above, the proximal and distal portion are to have different functions, they are provided as separate components. The prosthesis thus comprises a proximal portion 1 which is shaped to fit within the medullary canal of the metaphysis and a distal portion 2 which is shaped to fit within the medullary canal of the diaphysis. As will be described further below, the proximal portion 1 may be shaped to be a wedge fit within the metaphysis or a slightly smaller size may be selected to enable it to be cemented in place. The distal portion 2 is selected to fit within the diaphysis but not to be jammed or wedged therein so that it acts as a keel or 'anti-toggle' device.

Figures 2A, 2B, 2C:
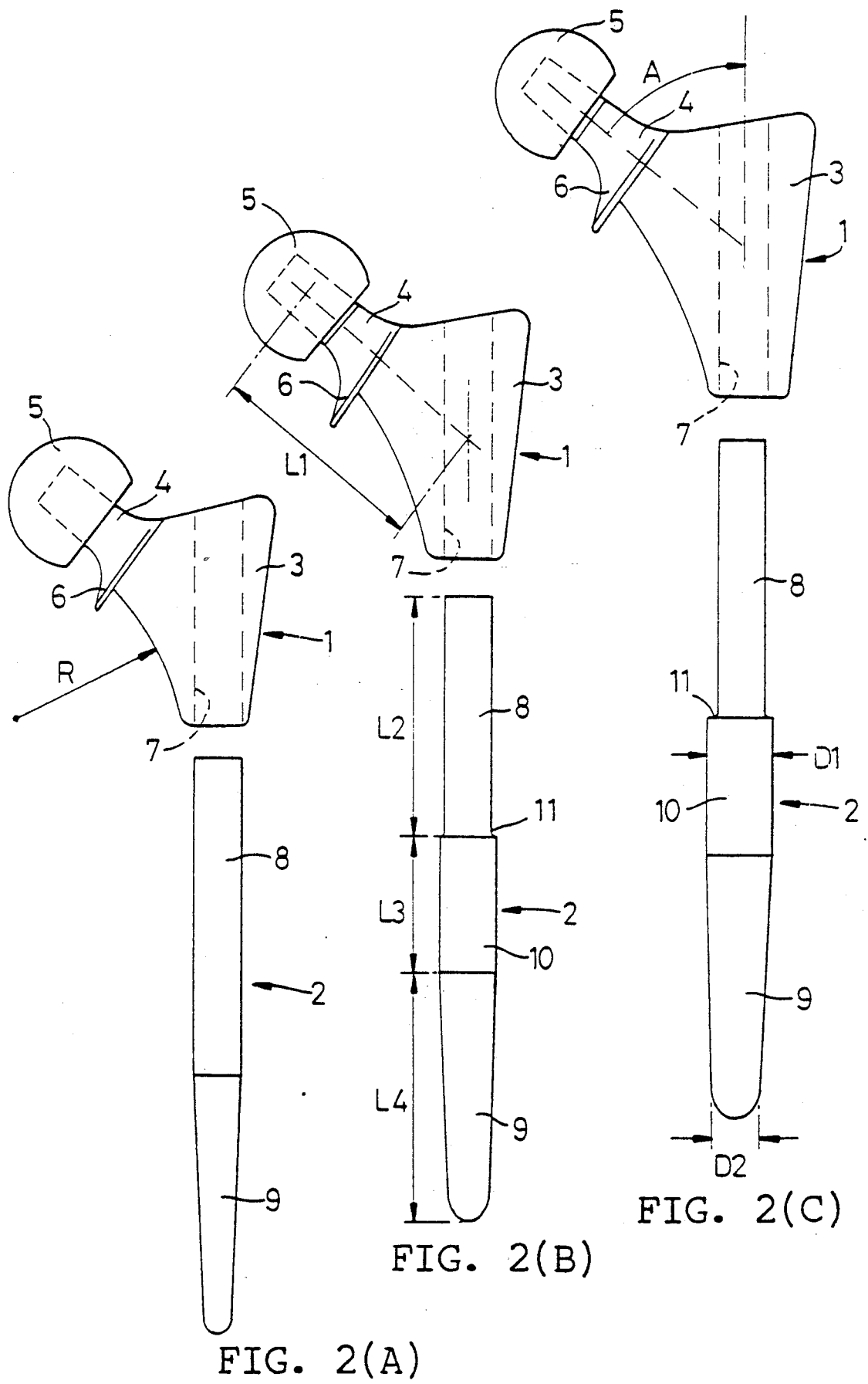
FIGS. 2A, 2B and 2C show three different sizes of a prosthesis according to an embodiment of the invention.

The proximal and distal portions 1 and 2 are arranged to fit together so portions of different sizes can be interchangeably fitted to one another to obtain the optimum fit within the bone. In particular, it is possible to fit a small proximal portion 1 as shown in FIG. 2A to a large distal portion as shown in FIG. 2C or a large proximal portion as shown in FIG. 2C to a small distal portion as shown in FIG. 2A. It will thus be appreciated that a wide range of sizes and combinations can be achieved with relatively few components compared to the prior art in which the proximal and distal portions are integrally formed.

The proximal portions 1 shown in FIG. 2 have a wedge portion 3 which has a tapered form to facilitate its fixation within the metaphysis by means of a wedge fit and a trunion neck 4 to which a head 5, such as the ball of a ball and socket joint, may be attached, e.g. by a screw thread. The effective length of the neck 4 may be adjusted in a known manner by providing a range of heads 5 having different length holes within which the neck 4 is fitted. In some cases, the neck 4 may also be provided with a collar 6 which, in use, engages an outer surface of the bone (see FIG. 3). A through-hole 7 is provided in the wedge portion 3 to enable it to be fitted to a distal portion 2.

The distal portion 2 shown in FIG. 2A has an elongate form and comprises a parallel sided shaft 8 for fitting within the hole of a proximal portion 1 and a tapered end portion 9 which fits within the medullary canal of the diaphysis. The larger size distal portions 1 shown in FIGS. 2B and 2C also have a parallel sided central portion 10 between the shaft 8 and end portion 9 with a shoulder 11 between the shaft 8 and the larger diameter central portion 10.

The through-holes 7 and shafts 8 are all of the same size (typically 12 mm in diameter) so that different size proximal and distal portions can be interchangeably fitted to one another. The shaft 8 is preferably a very close fit within the hole 7 but, as will be described below, it should preferably be a sliding fit therein. It is also possible to envisage an arrangement (not shown) in which a stem attached to the proximal portion fits within a hole in the distal portion.

It will be appreciated that a number of different dimensions may vary between proximal and distal portions of different sizes. For instance, in the proximal portion, the radius R, the length L1 and the angle A may be varied. In the distal portion, the lengths L2, L3 and L4 and the diameters D1 and D2 may be varied. A typical prosthesis kit may, for instance, comprise five proximal portions of different sizes and ten distal portions of differing lengths and/or diameters.

In addition to enabling different size proximal and distal portions to be interchangeably fitted together, a further important feature of the prothesis is that, when fitted together, the proximal and distal portions 1 and 2 may move relative to each other in a direction which corresponds to the length of the bone. As indicated above, this is provided by a sliding fit between the shaft 8 of the distal portion 2 and the through-hole 7 of the proximal portion 1.

This movement is desirable since it is known that (particularly with uncemented prostheses) there is some movement between the prosthesis and the bone, especially during the first 6 months following implantation. By allowing the proximal portion 1 to slide up and down the stem 8 of the distal portion 2 for a few millimeters (e.g. up to 5 mm) it is able to 'bed down' or settle into the metaphysis and constantly re-adjust its press fit with the metaphysial bone to ensure that proximal loading is ideally achieved. As the proximal portion 1 can slide on the stem 8 of the distal portion 2, this movement is possible without forcing the distal portion 2 further into the diaphysis which might cause the tip of the distal portion 2 to become wedged or jammed in the diaphysis. The proximal portion 1 may therefore move a few millimeters until it is optimally pressed into the metaphysis so that load transfer between the proximal portion and the proximal bone ensures the latter does not suffer from resorption.

Figure 3:
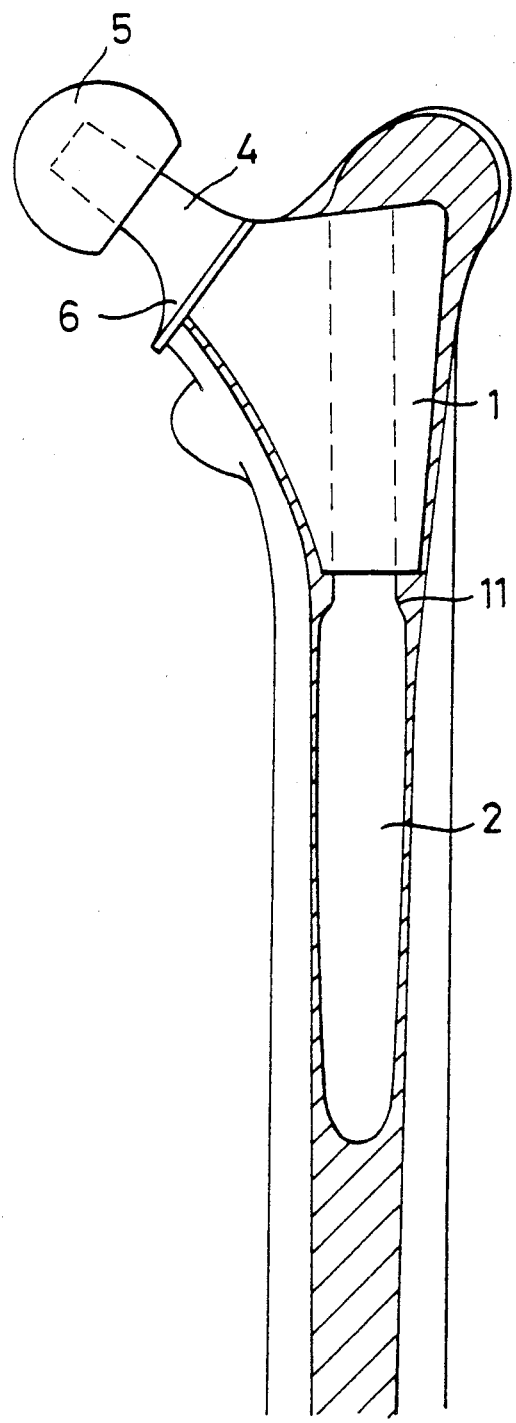
FIG. 3 shows one of the prostheses implanted in a femur.

The shoulder 11 of the distal portion 2 is arranged such that the proximal portion 1 may slide further onto the stem 8 of the distal portion 2 should the proximal portion 1 move within the metaphysis when load is applied to the prosthesis (see FIG. 3). The shoulder 11 does not therefore prevent the 'bedding down' movement discussed above.

It will be appreciated that if the proximal and distal portions 1 and 2 were rigidly connected (as in prior art integral prostheses) movement of the proximal portion 1 within the metephysis would be likely to force the distal portion 2 further into the diaphysis causing a jam fit between the distal portion 2 and the diaphysis and thus shifting the load transfer away from the proximal portion 1 which would lead to the problem of bone resorption discussed above.

FIG. 3 shows a prosthesis implanted within a femur. As discussed above, the proximal and distal portions 1 and 2 are selected to provide the desired or optimum fit within the metaphysis and the diaphysis of the bone. After removal of the head and neck of the bone, and removal of cancellous bone from within the metaphysis and the diaphysis, the prosthesis is implanted in the bone so that the proximal portion 1 fits within the metaphysis and the distal portion 2 fits within the diaphysis without being jammed therein.

The proximal portion 1 may be selected so that it is of a size which can be wedged within the metaphysis without the use of cement. For this purpose, the wedge portion 3 has a tapered form which corresponds to the tapered form of the medullary canal within the metaphysis once most or all of the cancellous bone has been removed therefrom. Alternatively, especially in elderly patients, it may be desired to cement the proximal portion 1 within the metaphysis. In this case, a slightly smaller proximal portion 1 is selected to leave room for the cement between the wedge portion 3 and the sides of the medullary canal into which it is to be secured. In both cases, the distal portion 2 is selected to fit within the medullary canal of the diaphysis without being wedged or cemented therein so that it acts merely as a keel or 'anti-toggle' device and, for the reasons discussed above, takes little of the load applied to the prosthesis.

In cases where the proximal portion 1 is to be cemented in place, the two-part construction of the prosthesis enables this to be done more easily since the distal portion 2 can be implanted first, before any cement has been applied to the bone, and then the proximal portion 1 can be cemented into the metaphysis and fitted to the distal portion 2. The problem of cement being carried down from the metaphysis into the medullary canal of the diaphysis as the prosthesis is inserted into the bone, as can happen during insertion of a one-piece prosthesis, is thus avoided.

It should be noted that even in cases in which the proximal portion 1 is cemented within the bone, there may still be some movement of the prosthesis when load is first applied to it. The provision for movement between the proximal and distal portion 1 and 2 is thus still desirable. Another advantage of the two-part construction of the prosthesis is its use in the management of fractures and revisions. If a bone has fractured around a loose prosthesis, for instance across the diaphysis, it is difficult to fit a new prosthesis whilst at the same time holding the fracture together. However, with the prosthesis described above, the distal portion 2 can first be fitted within the diaphysis to assist in hoding the fracture together. It is then much easier to fit the proximal portion 1 within the metaphysis. Thus, rather than fitting the two portions of the prosthesis together outside the bone and then implanting them as one unit, the distal portion 2 is first implanted on its own and the proximal portion 1 is then implanted within the metaphysis and fitted to the distal portion 2.

The invention is applicable to prostheses made of a wide variety of materials although the majority are these days made of titanium or an alloy thereof. The various surface treatments used in this field may also be applied to the prosthesis and in view of the two part construction it is a simple matter to form the proximal and distal portions 1 and 2 with different surface treatments should this is desired.

It will also be appreciated that the design of many known prostheses can be simply modified to provide the two-part construction described above and, preferably, also to allow the two portions to move relative to each other as described.

Other means for fitting the two portions together can also be envisaged as well as alternative means for permitting the said movement.

I claim:

1. A prosthesis for implantation in a bone comprising a proximal portion shaped to fit within the medullary canal of the metaphysis of the bone and to project from the end of the bone and an elongate distal portion defining a longitudinal axis and shaped to fit within the medullary canal of the diaphysis of the bone, the proximal and distal portions being separately formed and having complimentary engaging surfaces, parallel to each other and to the longitudinal axis, shaped so they may be fitted together in a manner which permits relatively free axial movement between the two portions while maintaining axial alignment of the portions, whereby the two portions may be independently selected to provide an optimum fit within the bone and, following implantation, are able to move freely relative to each other along said axis to maintain loading between the proximal portion and the bone.

2. A prosthesis as claimed in claim 1, wherein the proximal portion has a neck and means for attaching a head portion thereto.

3. A prosthesis as claimed in claim 2, wherein the neck is provided with a collar for engaging an outer surface of the bone.

4. A prosthesis as claimed in claim 1, wherein when the proximal and distal portions are fitted together, they are able to move relative to each other in the said direction by up to 5 mm.

5. A prosthesis as claimed in claim 1, wherein the proximal and distal portions are arranged to fit together by means of a stem on one portion which fits within a hole in the other portion, the stem being a sliding fit within the said hole.

6. A prosthesis as claimed in claim 5, wherein the hole is provided in the proximal portion and the stem on the distal portion.

7. A prosthesis as claimed in claim 2, which comprises a femoral component of an artificial hip joint, the proximal portion being shaped to fit within the metaphysis of a femur and the distal portion being shaped to extend into the medullary canal of the diaphysis of the femur.

8. A prosthesis system providing a selection of prostheses for implantation in a bone comprising:
a plurality of proximal portions of different sizes being shaped to fit within the medullary canal of the metaphysis of the bone and to project from the end of the bone and a plurality of elongate distal portions of different sizes each defining a longitudinal axis and being shaped to fit within the medullary canal of the diaphysis of the bone, the proximal and distal portions having complimentary engaging surfaces, parallel to each other and to the longitudinal axis, shaped so that they may be fitted together in any size combination in a manner which permits relatively free axial movement between the respective portions while maintaining axial alignment of the portions, whereby the two portions may be independently selected to provide optimum fit within the bone and, following implantation, are able to move relative to each other along said axis to maintain loading between the proximal portion and the bone.

9. A method of implanting a prosthesis within a bone, the prosthesis comprising a proximal portion shaped to fit within a medullary canal of the metaphysis of the bone and to project from an end of the bone and an elongate distal portion defining a longitudinal axis and shaped to fit within the medullary canal of a diaphysis of the bone, the proximal and distal portions being separately formed and having complimentary engaging surfaces, parallel to each other and to the longitudinal axis, shaped so they may be fitted together in a manner which permits relatively free axial movement between the two portions while maintaining axial alignment of the portions, whereby the two portions may be independently selected to provide an optimum fit within the bone and, following implantation, are able to move freely relative to each other along said axis to maintain loading between the proximal portion and the bone, the method comprising the steps of:
selecting the proximal portion and the distal portion to provide the optimum fit within the bone and implanting the distal portion first into the medullary canal of the diaphysis of the bone without the proximal portion and then implanting the proximal portion and fitting it together with the distal portion already implanted in the bone by means of said complimentary engaging surfaces, whereby the two portions, following implantation, are able to move freely relative to each other along said axis to maintain loading between the proximal portion and the bone.

10. A method as claimed in claim 9, in which the distal portion is first implanted without the use of cement and the proximal portion is then implanted using cement to help secure said proximal portion within the metaphysis of the bone, wherein the danger of cement being carried into the diaphysis of the bone is avoided.

* * * * *